(12) United States Patent
Cole

(10) Patent No.: US 11,147,939 B2
(45) Date of Patent: Oct. 19, 2021

(54) COMPACT DUAL LIMB DIAPHRAGM VALVE SYSTEM AND METHOD

(71) Applicant: KONINKLIJKE PHILIPS N.V., Eindhoven (NL)

(72) Inventor: Kenneth E. Cole, New Alexandria, PA (US)

(73) Assignee: Koninklijke Philips N.V., Eindhoven (NL)

(*) Notice: Subject to any disclaimer, the term of this patent is extended or adjusted under 35 U.S.C. 154(b) by 852 days.

(21) Appl. No.: 15/124,361

(22) PCT Filed: Mar. 3, 2015

(86) PCT No.: PCT/IB2015/051531
§ 371 (c)(1),
(2) Date: Sep. 8, 2016

(87) PCT Pub. No.: WO2015/136407
PCT Pub. Date: Sep. 17, 2015

(65) Prior Publication Data
US 2017/0014594 A1    Jan. 19, 2017

Related U.S. Application Data

(60) Provisional application No. 61/951,045, filed on Mar. 11, 2014.

(51) Int. Cl.
*A61M 16/20* (2006.01)
*F16K 7/17* (2006.01)
(Continued)

(52) U.S. Cl.
CPC ...... *A61M 16/206* (2014.02); *A61M 16/0066* (2013.01); *A61M 16/024* (2017.08);
(Continued)

(58) Field of Classification Search
CPC .......... A61M 16/0066; A61M 16/0069; A61M 16/024; A61M 16/0465; A61M 16/0666;
(Continued)

(56) References Cited

U.S. PATENT DOCUMENTS 3,610,236 A    10/1971    Smilg
3,633,605 A *  1/1972    Smith .................. F16K 31/1266
                                                      137/113

(Continued)

FOREIGN PATENT DOCUMENTS

CA    1286942       7/1987
EP    0143618 A2    6/1985
(Continued)

*Primary Examiner* — Timothy A Stanis
*Assistant Examiner* — Matthew R Moon
(74) *Attorney, Agent, or Firm* — Daniel H. Brean

(57) ABSTRACT

The system described comprises a respiratory therapy flow device, a respiratory circuit, and an exhalation valve. The device includes an exhalation pressure control port. The exhalation valve is removably engaged with the exhalation pressure control port and the respiratory circuit. The valve comprises a lid, a diaphragm, and a housing body. The housing body comprises a ramped lock configured to engage the respiratory therapy flow device at the exhalation pressure control port. Responsive to an engagement between the valve and the exhalation pressure control port, the lid forms a compression seal with the exhalation pressure control port, the diaphragm forms a compression seal with the lid, and the diaphragm is selectively controlled via gas pressure received through the exhalation pressure control port such that gas in the respiratory circuit flows to the ambient atmosphere during exhalation by the subject.

21 Claims, 6 Drawing Sheets

(51) Int. Cl.
*A61M 16/00* (2006.01)
*A61M 16/04* (2006.01)
*A61M 16/06* (2006.01)
*A61M 16/16* (2006.01)
*A61M 16/10* (2006.01)

(52) U.S. Cl.
CPC .... *A61M 16/0465* (2013.01); *A61M 16/0666* (2013.01); *F16K 7/17* (2013.01); *A61M 16/0069* (2014.02); *A61M 16/161* (2014.02); *A61M 16/205* (2014.02); *A61M 2016/003* (2013.01); *A61M 2016/0027* (2013.01); *A61M 2016/102* (2013.01); *A61M 2205/3334* (2013.01); *A61M 2205/3365* (2013.01); *A61M 2205/3368* (2013.01); *A61M 2205/502* (2013.01); *A61M 2205/52* (2013.01)

(58) Field of Classification Search
CPC .............. A61M 16/161; A61M 16/205; A61M 16/206; A61M 2016/0027; A61M 2016/003; A61M 2016/102; A61M 2205/3334; A61M 2205/3365; A61M 2205/3368; A61M 2205/502; A61M 2205/52; F16K 7/17; F16K 15/144; F16K 31/1266

See application file for complete search history.

(56) References Cited

U.S. PATENT DOCUMENTS

| | | | |
|---|---|---|---|
| 4,241,756 A | 12/1980 | Bennett | |
| 5,020,532 A | 6/1991 | Mahoney | |
| 5,484,270 A * | 1/1996 | Adahan | A61M 16/20 128/205.13 |
| 5,937,855 A | 8/1999 | Zdrojkowski | |
| 6,283,122 B1 | 9/2001 | Adahan | |
| 9,616,174 B2 * | 4/2017 | Fabien | A61M 5/20 |
| 2002/0014239 A1 | 2/2002 | Chalvignac | |
| 2006/0076016 A1 | 4/2006 | Hewitt | |
| 2013/0008444 A1 | 1/2013 | Chalvignac | |
| 2017/0014594 A1 | 1/2017 | Cole | |

FOREIGN PATENT DOCUMENTS

| | | | |
|---|---|---|---|
| GB | 2487089 A | 7/2012 | |
| WO | WO-2009089807 A1 * | 7/2009 | ............ A61M 16/06 |
| WO | WO2009089807 A1 | 7/2009 | |
| WO | WO-2012020387 A1 * | 2/2012 | .......... A61M 16/204 |

* cited by examiner

COMPACT DUAL LIMB DIAPHRAGM VALVE SYSTEM AND METHOD

CROSS-REFERENCE TO RELATED APPLICATIONS

This patent application claims the priority benefit under 35 U.S.C. § 371 of international patent application no. PCT/IB2015/051531, filed Mar. 3, 2015, which claims the priority benefit under 35 U.S.C. § 119(e) of U.S. Provisional Application No. 61/951,045 filed on Mar. 11, 2014, the contents of which are herein incorporated by reference.

BACKGROUND OF THE INVENTION

1. Field of the Invention

The present disclosure pertains to a pressure support system configured to provide pressure support to a subject.

2. Description of the Related Art

It is common to treat patients with respiratory therapy. Some respiratory therapy systems use a respiratory support circuit. Different types of respiratory support circuits may be used for different types of respiratory therapy. Respiratory support circuits may include one or more of a single-limb configuration, a dual-limb configuration, and/or other configurations.

SUMMARY OF THE INVENTION

Accordingly, one aspect of the present disclosure relates to a pressure support system configured to provide pressure support to a subject. The system comprises a respiratory therapy flow device, a respiratory circuit, an exhalation valve, and/or other components. The respiratory therapy flow device is configured to generate a pressurized flow of breathable gas for delivery to an airway of the subject in accordance with a pressure support therapy regime. The respiratory therapy flow device includes an exhalation pressure control port. The respiratory circuit is configured to conduct the pressurized flow of breathable gas to the subject and conduct exhaled gas from the subject. The exhalation valve is configured to be removably engaged with the exhalation pressure control port and the respiratory circuit. The valve comprises a lid, a diaphragm, and a housing body. The housing body is configured to house the diaphragm and receive the lid. The housing body comprises a lock configured to engage the respiratory therapy flow device at the exhalation pressure control port. An engagement between the valve and the exhalation pressure control port causes the lid to form a compression seal with the exhalation pressure control port, the diaphragm to form a compression seal with the lid, and the diaphragm to be selectively controlled via gas pressure received through the exhalation pressure control port such that gas in the respiratory circuit flows to the ambient atmosphere during exhalation by the subject.

Another aspect of the present disclosure relates to a method for providing pressure support to a subject with a pressure support system. The system comprises a respiratory flow device that includes an exhalation pressure control port, a respiratory circuit, and an exhalation valve that includes a lid, a diaphragm, and a housing body. The housing body comprises a lock. The method comprises generating, with the respiratory therapy flow device, a pressurized flow of breathable gas for delivery to an airway of the subject in accordance with a pressure support therapy regime; conducting, with the respiratory circuit, the pressurized flow of breathable gas to the subject; conducting, with the respiratory circuit, exhaled gas from the subject; housing the diaphragm and receiving the lid with the housing body; removably engaging the valve with the exhalation pressure control port and the respiratory circuit, wherein removably engaging includes: engaging, with the lock, the respiratory therapy flow device at the exhalation pressure control port; causing the lid to form a compression seal with the exhalation pressure control port; and causing the diaphragm to form a compression seal with the lid; and, selectively controlling the diaphragm via gas pressure received through the exhalation pressure control port such that gas in the respiratory circuit flows to the ambient atmosphere during exhalation by the subject.

Yet another aspect of the present disclosure relates to a pressure support system configured to provide pressure support to a subject. The system comprises means for generating a pressurized flow of breathable gas for delivery to an airway of the subject in accordance with a pressure support therapy regime. The means for generating includes an exhalation pressure control port. The system comprises means for conducting the pressurized flow of breathable gas to the subject and conducting exhaled gas from the subject; and means for removably engaging the exhalation pressure control port and the means for conducting. The means for removably engaging comprises a lid, a diaphragm, and a housing body. The housing body is configured to house the diaphragm and receive the lid. The housing body comprises a locking configured to engage the means for generating at the exhalation pressure control port such that and engagement between the means for removably engaging and the exhalation pressure control port causes the lid to form a compression seal with the exhalation pressure control port, the diaphragm to form a compression seal with the lid, and the diaphragm to be selectively controlled via gas pressure received through the exhalation pressure control port such that gas in the means for conducting flows to the ambient atmosphere during exhalation by the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
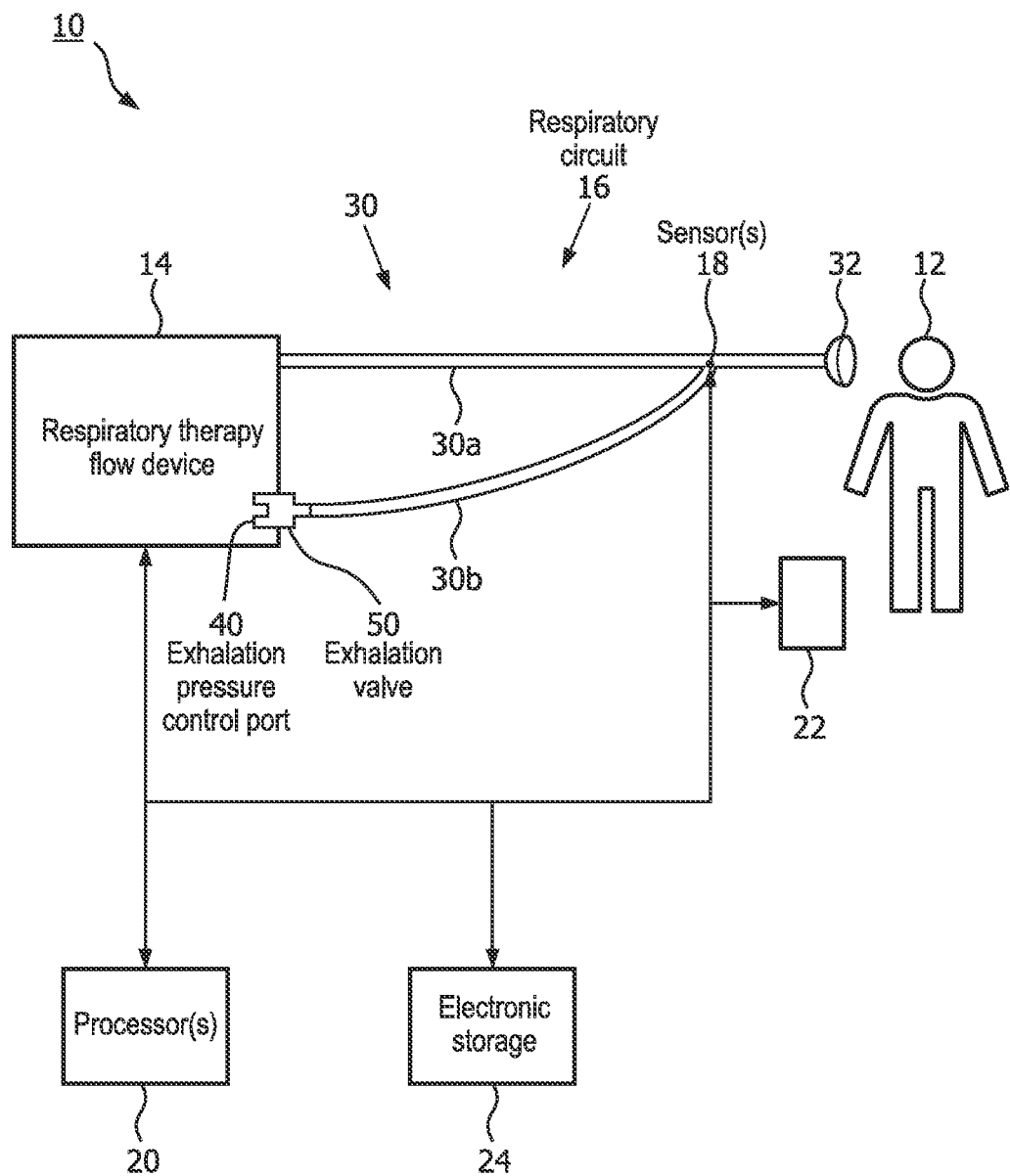
FIG. 1 schematically illustrates a pressure support system configured to provide pressure support to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a pressure support system 10 configured to provide pressure support to a subject 12. In some embodiments, system 10 includes one or more of a respiratory therapy flow device 14, a respiratory circuit 16, an exhalation valve 50, a sensor 18, a processor 20, a user interface 22, electronic storage 24, and/or other components. System 10 is configured to be interchanged between two system configurations: (1) a dual-limb system with two gas carrying conduits (e.g., an inspiratory limb and an expiratory limb); and (2) a single-limb system that includes only the inspiratory limb (shown in FIG. 2).

In the dual-limb configuration, exhalation valve 50 is disposed on the housing of respiratory therapy flow device 14 and coupled with an exhalation pressure control port 40. An expiratory limb 30b of respiratory circuit 16 also couples with valve 50 such that exhaust gas from subject 12 flows to the atmosphere following a path through valve 50. Respiratory therapy flow device 14 provides pressurized gas to valve 50 to control gas exhaled by subject 12 through valve 50 to regulate the flow of exhaust gas to the atmosphere.

Figure 2:
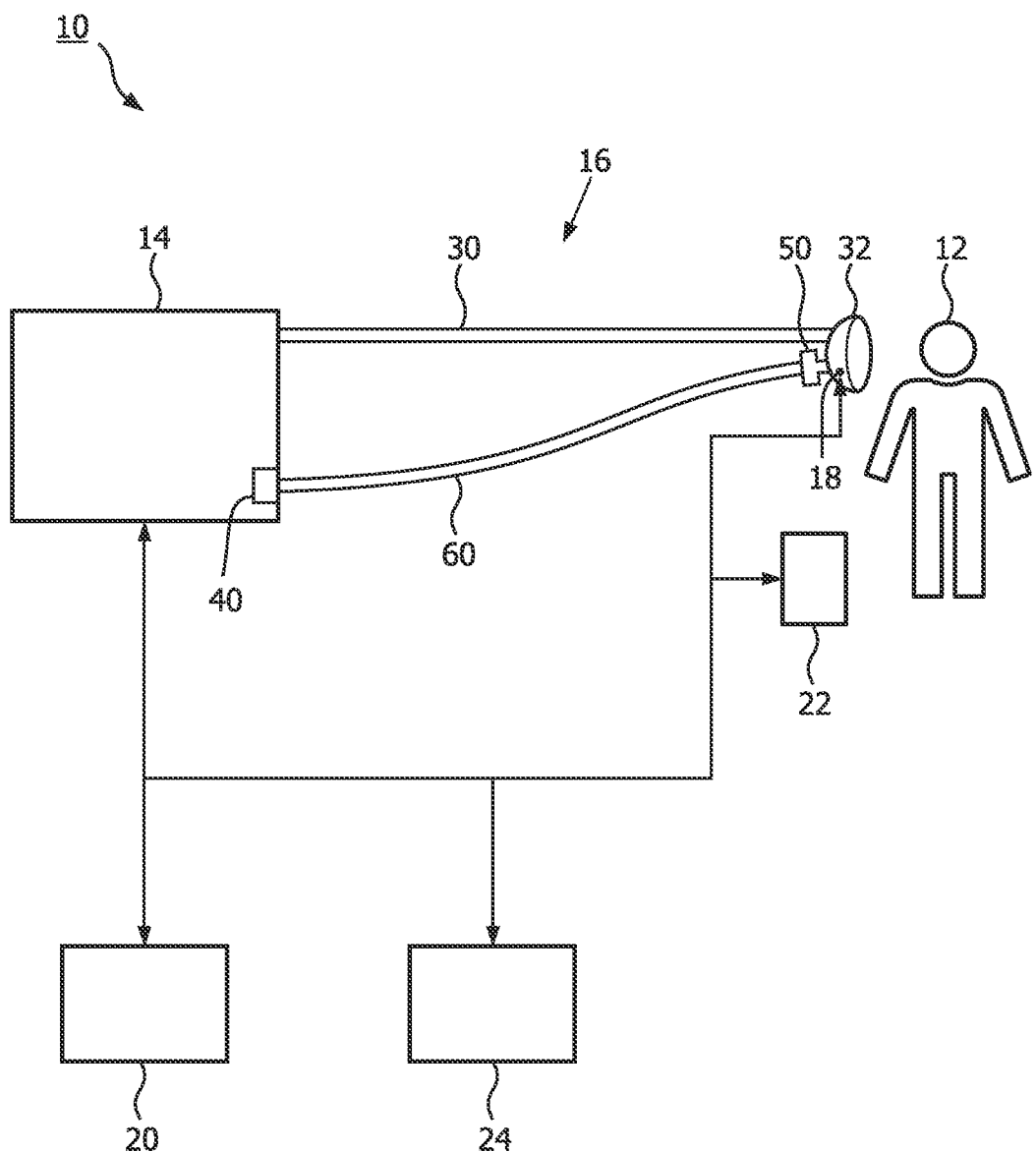
FIG. 2 illustrates the system with a single limb respiratory circuit.

As shown in FIG. 2, in the single-limb a configuration, valve 50 is removed from the housing of respiratory therapy flow device 14 and a pressure control line 60 connects exhalation pressure control port 40 to valve 50 to regulate the flow of exhaust gas to the atmosphere. This allows pressure provided via exhalation pressure control port 40 to control valve 50 whether valve 50 is located on the respiratory therapy flow device housing (as shown in FIG. 1) or at the end of respiratory circuit 16 (shown in FIG. 2).

Such valves in traditional dual-limb circuits are not neatly integrated into the respiratory therapy flow device, and are typically their own standalone entity. System 10 is configured such that that when valve 50 is connected to respiratory circuit 16 in a single-limb configuration, valve 50 appears as part of the circuit (FIG. 2), but is easily docked becoming integral to respiratory therapy flow device 14 (FIG. 1).

Respiratory therapy flow device 14 is configured to generate a pressurized flow of breathable gas for delivery to an airway of subject 12 in accordance with a pressure support therapy regime. Respiratory therapy flow device 14 may be and/or include one or more of a pressure generator, a ventilator, a positive airway pressure device (PAP/CPAP/BiPAP®/etc.), and/or other devices. Respiratory therapy flow device 14 is configured to provide the pressurized flow of breathable gas for delivery to the airway of subject 12 via respiratory circuit 16. Respiratory therapy flow device 14 receives a flow of gas from a gas source, such as the ambient atmosphere, and elevates the pressure of that gas for delivery to subject 12. Respiratory therapy flow device 14 includes any device, such as, for example, a pump, blower, piston, or bellows, that is capable of elevating the pressure of the received gas for delivery to subject 12. Respiratory therapy flow device 14 may include a motor. Respiratory therapy flow device 14 may comprise one or more valves for controlling the flow of gas. The present disclosure also contemplates controlling the operating speed of the blower, either alone or in combination with such valves, to control the gas provided to subject 12.

Respiratory therapy flow device 14 may be configured to adjust pressure levels, flow, humidity, velocity, acceleration, and/or other parameters of the pressurized flow of breathable gas in substantial synchronization with the breathing phases (e.g., inhalation/exhalation) of subject 12. Subject 12 may or may not initiate one or more phases of respiration. Respiratory therapy may be implemented as pressure control, pressure support, and/or volume control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Other schemes for providing respiratory therapy through the delivery of the pressurized flow of breathable gas are contemplated.

Respiratory therapy flow device 14 is configured to deliver a control flow of pressurized gas through exhalation pressure control port 40. Exhalation pressure control port 40 is a port in respiratory therapy flow device 14 that is separate from the coupling between respiratory circuit 16 and respiratory therapy flow device 14 where respiratory circuit 16 receives the pressurized flow of breathable gas. The control flow of gas may be produced by, for example, the pump, blower, piston, or bellows of respiratory therapy flow device 14. The control flow of gas may be produced separately from and/or be separated from the pressurized flow of breathable gas by one or more valves for controlling the flow of gas included in respiratory therapy flow device 14. The present disclosure also contemplates controlling the motor of the respiratory therapy flow device 14 and the operating speed of the blower, either alone or in combination with such valves, to produce the control flow of pressurized gas provided via exhalation pressure control port 40.

Respiratory circuit 16 is configured to communicate the pressurized flow of breathable gas to the airway of subject 12. In some embodiments, respiratory circuit 16 is configured to communicate the pressurized flow of breathable gas from respiratory therapy flow device 14 to the airway of subject 12. As such, respiratory circuit 16 comprises one or more of a conduit 30, an interface appliance 32, and/or other components.

Interface appliance 32 is configured to deliver the flow of gas to the airway of subject 12. In some embodiments, interface appliance 32 is configured to be non-invasively engaged by the nose and/or mouth of subject 12. Non-invasive engagement comprises removably engaging one or more external orifices of the airway of subject 12 (e.g., nostrils and/or mouth) to communicate gas between the airway of subject 12 and interface appliance 32. In some embodiments, interface appliance 32 is removably coupled to conduit 30. Interface appliance 32 may be removed for cleaning and/or for other purposes. Some examples of non-invasive interface appliance 32 may comprise, for example, a nasal cannula, a nasal mask, a nasal/oral mask, a full face mask, a total face mask, and/or other interface appliances that communicate a flow of gas with an airway of a subject. In some embodiments, interface appliance 32 is invasive. Some examples of invasive interface appliances that may comprise interface appliance 32 are endotracheal tubes, tracheostomy tubes, and or other devices. The present disclosure is not limited to these non-invasive and/or invasive examples, and contemplates delivery of the flow of gas to the subject using any interface appliance.

Respiratory circuit 16 may further comprise optional valves and/or orifices that serve to regulate an amount of inspiratory pressure, an inspiratory flow rate, an expiratory pressure, an expiratory flow rate, and/or other parameters of the pressurized flow of breathable gas that is delivered to the airway of subject 12. In some embodiments, the inspiratory pressure, the expiratory pressure, or both, may be regulated by valves and/or orifices in interface appliance 32 and/or conduits 30. For example, if subject 12 requires greater flow than system 10 is able to deliver, then the use of one-way inspiration valves will allow the subject 12 to freely inhale additional ambient air. As another example, in the case of a patient that requires expiratory resistance to counter their intrinsic positive end expiratory pressure (PEEP), then the use of fixed and/or regulated expiratory orifices may provide additional positive expiratory pressure (PEP).

Respiratory circuit 16 is illustrated in FIG. 1 as a dual-limbed interface for the delivery of the pressurized flow of gas to the airway of the subject. As shown in FIG. 1, respiratory circuit 16 has a first limb 30*a* configured to provide the pressurized flow of breathable gas to the airway of subject 12, and a second limb 30*b* configured to selectively exhaust exhaled gases. As shown in FIG. 2, the scope of this disclosure also includes single-limbed circuits. The limbs (e.g., conduits 30 shown in FIG. 1 and/or FIG. 2) may be flexible gas delivery circuits configured not only for the transport of gases but to communicate indications of the spontaneous respiration of subject 12 in order to trigger a flow of gas (described below). Conduits 30 are configured to convey the pressurized flow of breathable gas to interface appliance 32. Conduits 30 may be a flexible length of hose, and/or other conduits that place interface appliance 32 in fluid communication with other components of system 10 (e.g., respiratory therapy flow device 14). Conduits 30 have a sufficient diameter to effectively deliver the pressurized flow of breathable gas with a flow rate and/or pressure that maintains adequate pressure support ventilation. In some implementations, respiratory circuit 16 may include a dual lumen type conduit 30 where a small bore lumen is used to sense (e.g., see the descriptions of sensor 18 and processor 20 below) the respiration pattern of subject 12 and control the pressurized flow of breathable gas in synchrony with the spontaneous breathing of the subject.

In single-limb embodiments (FIG. 2), valve 50 is coupled to a first end of a pressure control line 60. A second end of pressure control line 60 is coupled to respiratory therapy flow device 14 at exhalation pressure control port 40 separately from respiratory circuit 16. In some embodiments, the second end of pressure control line 60 may be coupled to a pressure source other than respiratory therapy flow device 14. Pressure control line 60 may be a flexible length of hose, or other conduit, that places valve 50 in fluid communication with exhalation pressure control port 40. Pressure control line 60 is configured to convey a control flow of gas (e.g., air) to valve 50. In some embodiments, the control flow of gas delivered to pressure control line 60 is separate from the pressurized flow of breathable gas delivered to conduit 30. In some embodiments, the control flow of gas generated by respiratory therapy flow device 14 is controlled by one or more valves within respiratory therapy flow device 14, processor 20, and/or other components of system 10. Valve 50 is configured to receive the control flow of gas from respiratory therapy flow device 14 via pressure control line 60.

Figure 3:
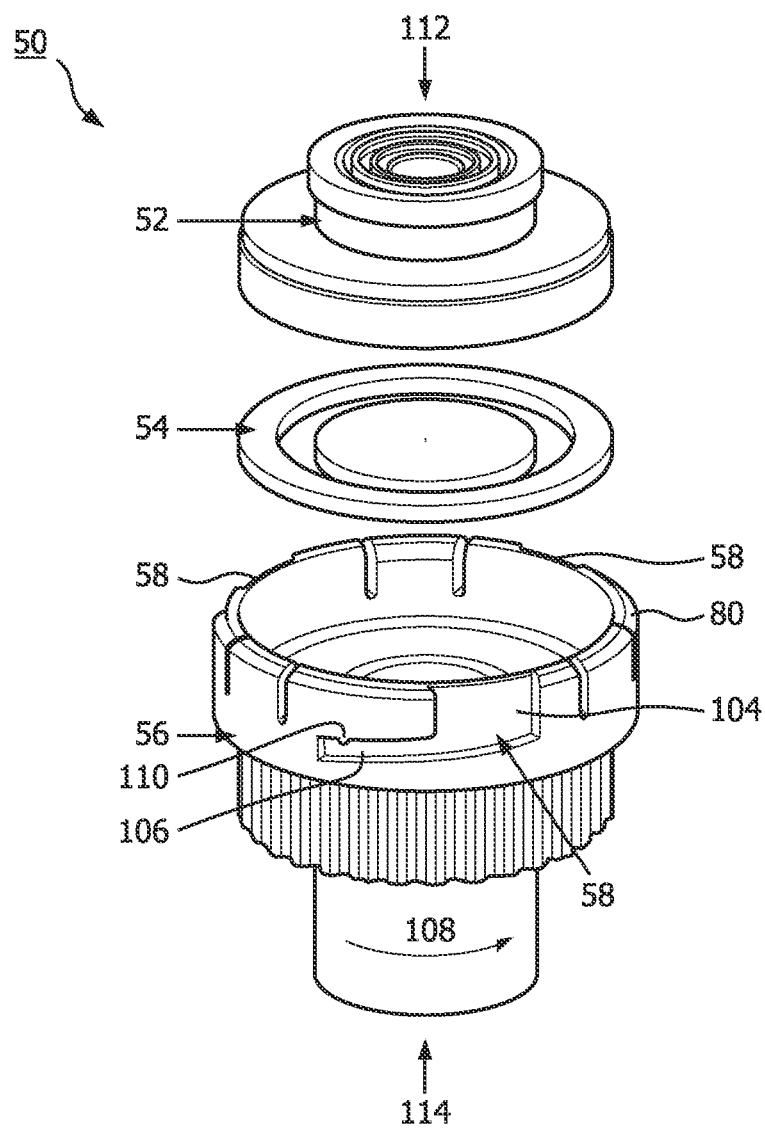
FIG. 3 illustrates a first view of an exhalation valve.
Figure 4:
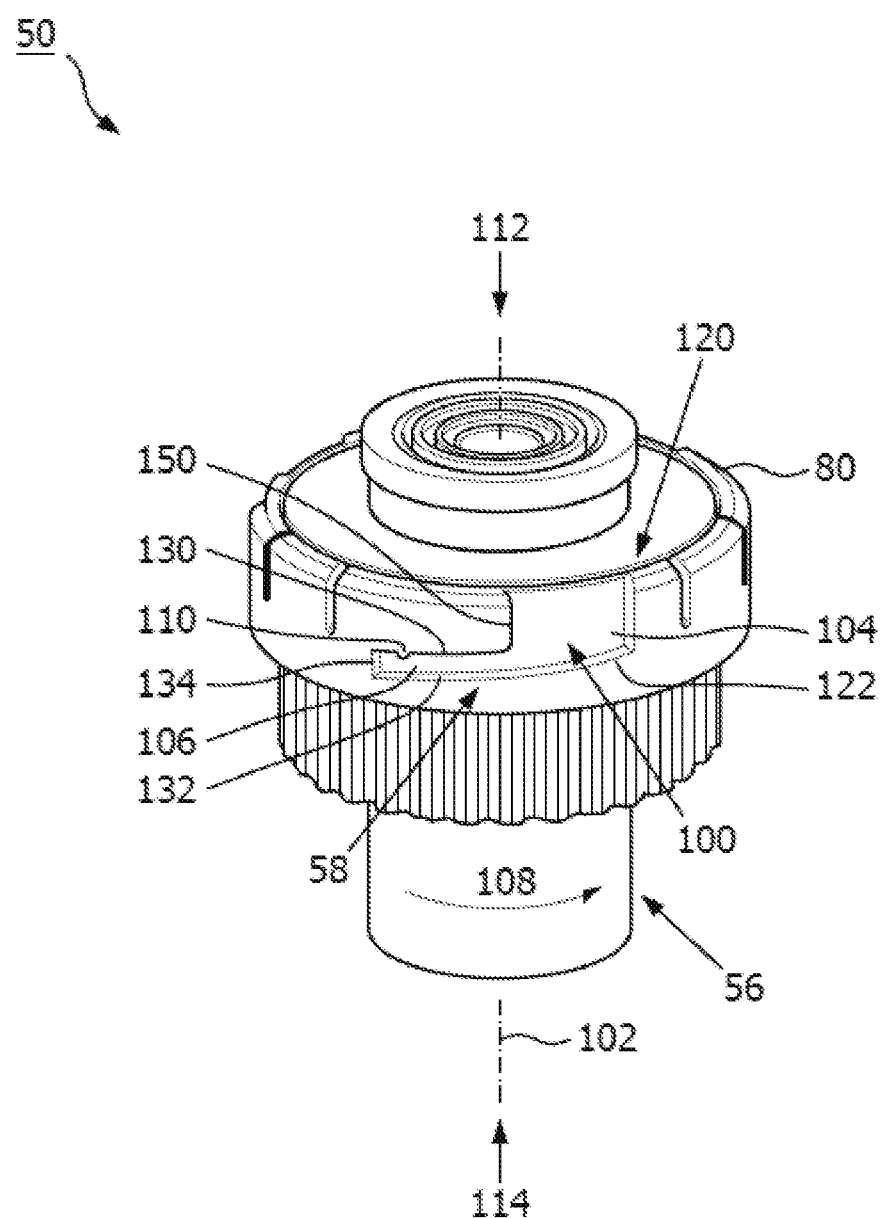
FIG. 4 illustrates a second view of an exhalation valve.
Figure 5:
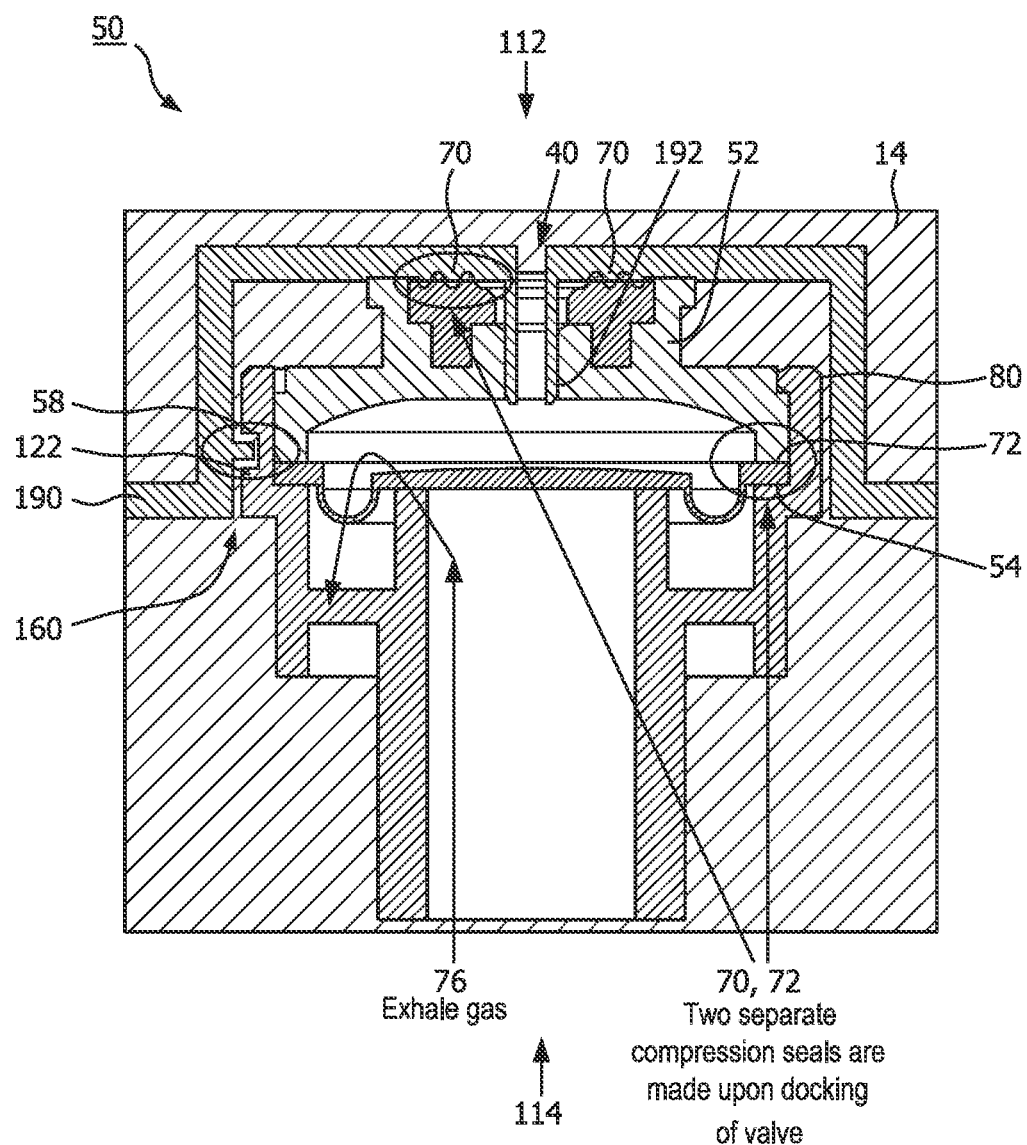
FIG. 5 illustrates a section view of an exhalation valve in an exhalation pressure control port.

Exhalation valve 50 is configured to be removably engaged with exhalation pressure control port 40 and respiratory circuit 16. FIG. 3-5 illustrate valve 50. As illustrated in FIG. 3, valve 50 comprises a lid 52, a diaphragm 54, a housing body 56, and/or other components. As illustrated in FIG. 3 and FIG. 4, housing body 56 is configured to house diaphragm 54 and receive lid 52. Lid 52 is retained to housing body 58 in such a way that during engagement to a housing 190 of respiratory therapy flow device 14 (see FIG. 5) at exhalation pressure control port 40, for example, compression of diaphragm 54 is primarily axial, with minimal to no torsion, so as to not substantially deform diaphragm 54. As illustrated in FIG. 5, an engagement between valve 50 and exhalation pressure control port 40 (respiratory circuit 16 may be engaged with valve 50 at an opposite end) causes lid 52 to form a compression seal 70 with exhalation pressure control port 40, diaphragm 54 to form a compression seal 72 with the lid, and diaphragm 54 to be selectively controlled via gas pressure received through exhalation pressure control port 40 such that gas in respiratory circuit 16 flows 76 to the ambient atmosphere during exhalation by subject 12 (not shown).

As illustrated in FIG. 4, housing body 56 includes a ramped lock 58 configured to engage respiratory therapy flow device 14 (not shown) at exhalation pressure control port 40 (not shown). Ramped lock 58 drives valve 50 into exhalation pressure control port 40. In some embodiments, ramped lock 58 comprises at least one individual ramped lock. In some embodiments, ramped lock 58 comprises three individual ramped locks spaced approximately equidistant from each other on an outer circumference 80 of housing body 56. This is not intended to be limiting. Ramped locks 58 may comprise any number and or type of individual locks positioned in multiple locations on outer circumference 80 as long as system 10 functions as described herein. The ramped lock(s) cause valve 50 to make the seals described above (e.g., lid 52 with exhalation pressure control port 40 and diaphragm 54 to lid 52, see reference numbers 70 and 72 in FIG. 5). The three piece assembly design of valve 50 allows for a direct, axial compression of both seals, reducing and/or eliminating twist on diaphragm 54, thus reducing and/or eliminating deformation of diaphragm 54, and allowing for a more consistent performance relative to prior art valves.

Ramped lock 58 forms a channel 100 in housing body 56 that has a depth that extends from outer circumference 80 toward a central axis 102 of valve 50. Channel 100 comprises an alignment portion 104 and a compression locking portion 106. Alignment portion 104 is configured to orient ramped lock 58 with respect to corresponding locking features 160 in exhalation pressure control port 40 (shown in FIG. 5). Alignment portion 104 extends from a first end 112 of housing body 56 toward a second end 114 of housing body 56 substantially parallel to axis 102 on outer circumference 80. Alignment portion 104 has an open end 120 at first end 112 of housing body 56 and a closed end 122 toward second end 114. Compression locking portion 106 extends from and edge 150 of closed end 122 around housing body 56 on outer circumference 80. As compression locking portion 106 extends from alignment portion 104, compression locking portion 106 declines away from first end 112 of housing body 56. Compression locking portion 106 is configured to rotate 108 with respect to corresponding locking features 160 (FIG. 5) in exhalation pressure control port 40. Corresponding locking features 160 in exhalation pressure control port 40 ride in compression locking portion 106 during rotation and lock on a locking protrusion 110 of compression locking portion 106. Locking protrusion 110 extends into compression locking portion 106 from a first side 130 of compression locking portion 106 toward a second side 132 substantially parallel to axis 102. Locking protrusion is located near an end 134 of compression locking portion 106. In some implementations, valve 50 is configured such that ramped lock 58 of housing body 56 is a cam lock, and/or other locks.

By way of a non-limiting example, a user may rotate valve 50 in exhalation pressure control port 40 until alignment portion 104 aligns with corresponding locking features 160 (FIG. 5) in exhalation pressure control port 40. The user may push (e.g., causing the compression seals described herein) valve 50 into exhalation pressure control port 40 until corresponding locking features 160 reach and/or nearly reach closed end 122 of alignment portion 104 and then rotate 108 valve 50 such that corresponding locking features 160 of exhalation control port 40 ride in compression locking portion 106 until they lock on locking protrusion 110. Ramped lock 58 drives the valve into exhalation pressure control port 40. When locked via locking protrusion 110, valve 50 maintains the compression seal between the diaphragm 54 and lid 52, and the compression seal lid 52 makes with exhalation pressure control port 40.

FIG. 5 illustrates a section view of valve 50 in exhalation pressure control port 40. Exhalation pressure control port 40 may be formed in a housing 190 of respiratory therapy flow device 14, for example. Exhalation pressure control port 40 may include a male connector 192 configured to couple with lid 52 of valve 50, one or more locking features 160 that correspond to ramped lock 58, and/or other components. Corresponding locking features may include, for example, a protrusion configured to ride in the channel 104, 106 formed by ramped lock 58 and/or engage locking protrusion 110, and/or other features. Exhalation pressure control port 40 may be configured to receive, accept, engage, and/or otherwise couple with pressure control lines for other active circuits when valve 50 is not in use (engaged) with respiratory therapy flow device 14. Respiratory therapy flow device 14 may deliver the control flow of gas at a pilot pressure via a proportional valve controlled by processor 20 (not shown in FIG. 5) through male connector 192 to control exhalation by subject 12 (not shown in FIG. 5). The pilot pressure pushes on diaphragm 54 and controls the exhalation pressure necessary to displace diaphragm 54 and allow gas to be exhaled 76 to atmosphere.

FIG. 1, sensor 18 is configured to generate output signals conveying information related to one or more gas parameters of the pressurized flow of breathable gas within system 10. The one or more parameters of the gas within system 10 may comprise gas parameters related to the pressurized flow of breathable gas, breathing parameters related to respiration of subject 12, and/or other parameters. Sensor 18 may comprise one or more sensors that measure such parameters directly (e.g., through fluid communication with the flow of gas in interface appliance 32 and/or conduit 30). Sensor 18 may comprise one or more sensors that generate output signals related to the one or more parameters indirectly. For example, sensor 18 may comprise one or more sensors configured to generate an output based on an operating parameter of respiratory therapy flow device 14 (e.g., motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, concentration of one or more constituents (e.g., the concentration of oxygen), and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters.

In some embodiments, sensor 18 comprises one or more flow rate sensors configured to generate output signals conveying information related to the flow rate of the pressurized flow of breathable gas. Flow rate sensors suitable for use as sensor 18 may include, for example, mechanical flow rate sensors, pressure based flow rate sensors, optical flow rate sensors, thermal mass flow rate sensors, magnetic flow rate sensors, and/or other flow rate sensors.

In some embodiments, sensor 18 comprises one or more pressure sensors configured to generate output signals conveying information related to the pressure of the pressurized flow of breathable gas. Pressure sensors suitable for use as sensor 18 may include, for example, mechanical sensors, capacitive sensors, electromagnetic sensors, piezoelectric sensors, optical sensors, dual lumen sensors, and/or other pressure sensors.

In some embodiments, sensor 18 may comprise one or more oxygen sensors configured to generate output signals related to the concentration of oxygen in the pressurized flow of breathable gas delivered to and/or exhaled by subject 12.

Although sensor 18 is illustrated in FIG. 1 at a single location in system 10, this is not intended to be limiting. Sensor 18 may comprise sensors disposed in a plurality of locations, such as for example, at various locations within (or in communication with) conduit 30, within respiratory therapy flow device 14, within (or in communication with) interface appliance 32, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., respiratory therapy flow device 14), or processor 20 may represent processing functionality of a plurality of devices operating in coordination.

Processor 20 is configured, by computer readable instructions, to control respiratory therapy flow device 14 and/or other components of system 10 to deliver the pressurized flow of breathable gas to the subject according to a pressure support therapy regime. Pressure support therapy may be used to maintain an open airway in subject 12 so that oxygen, carbon dioxide, and/or other gases may be exchanged more easily, requiring little and/or no effort from subject 12. Processor 20 may be configured to control the system components based on the output signals from sensor 18 and/or other information.

By way of non-limiting example, processor 20 may control the components of system 10 such that the pressure support provided to subject 12 via the pressurized flow of breathable gas comprises continuous positive airway pressure support (CPAP), bi-level positive airway pressure support (BPAP), proportional positive airway pressure support (PPAP), and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), system 10 may apply variable pressure support in which the amount of pressure delivered to the patient during inhalation and/or during exhalation is determined and delivered on a breath by breath basis.

Processor 20 is configured such that controlling respiratory therapy flow device 14 and/or other components of system 10 to deliver the pressurized flow of breathable gas to subject 12 according to a pressure support therapy regime may include determining inhalation phases and/or exhalation phases during breathing of subject 12 based on the output signals and/or other information. Controlling respiratory therapy flow device 14 and/or other components of system 10 may include controlling one or more valves associated with respiratory therapy flow device 14, conduits 30, interface appliance 32, and/or other components of system 10.

In some embodiments, processor 20 is configured to control respiratory therapy flow device 14 to deliver a control flow of pressurized gas through exhalation pressure control port 40. The control flow of gas may be controlled separately from the pressurized flow of breathable gas delivered to subject 12. In some embodiments, processor 20 is configured to control respiratory therapy flow device 14 to deliver the control flow of gas at a pilot pressure via a proportional valve controlled by processor 20 to control exhalation by subject 12. The pilot pressure pushes on diaphragm 54 (FIG. 3) and controls the exhalation pressure necessary to displace diaphragm 54 and allow gas to be exhaled 76 (FIG. 5) to atmosphere.

User interface 22 is configured to provide an interface between system 10 and subject 12 and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of respiratory therapy flow device 14, processor 20, and/or other components of system 10. For example, a user may specify one or more therapy regimes and/or therapy regime set points that are to be delivered to subject 12 using user interface 22. As another example, therapy pressures, the breath rate of subject 12, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with respiratory therapy flow device 14, and/or processor 20.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function as described herein. Electronic storage 24 may be (in whole or in part) a separate component within system 10, or electronic storage 24 may be provided (in whole or in part) integrally with one or more other components of system 10 (e.g., user interface 22, processor 20, etc.).

Information determined by processor 20 and/or stored by electronic storage 24 may comprise information related to respiration of subject 12, and/or other information. The information stored by electronic storage 24 may be viewed via user interface 22, viewed by connecting (wired and/or wireless) to a separate computer, and/or other via other methods. The information stored by electronic storage 24 may be used, for example, to adjust therapy settings, used by a doctor to make medical decisions, and/or for other uses.

Figure 6:
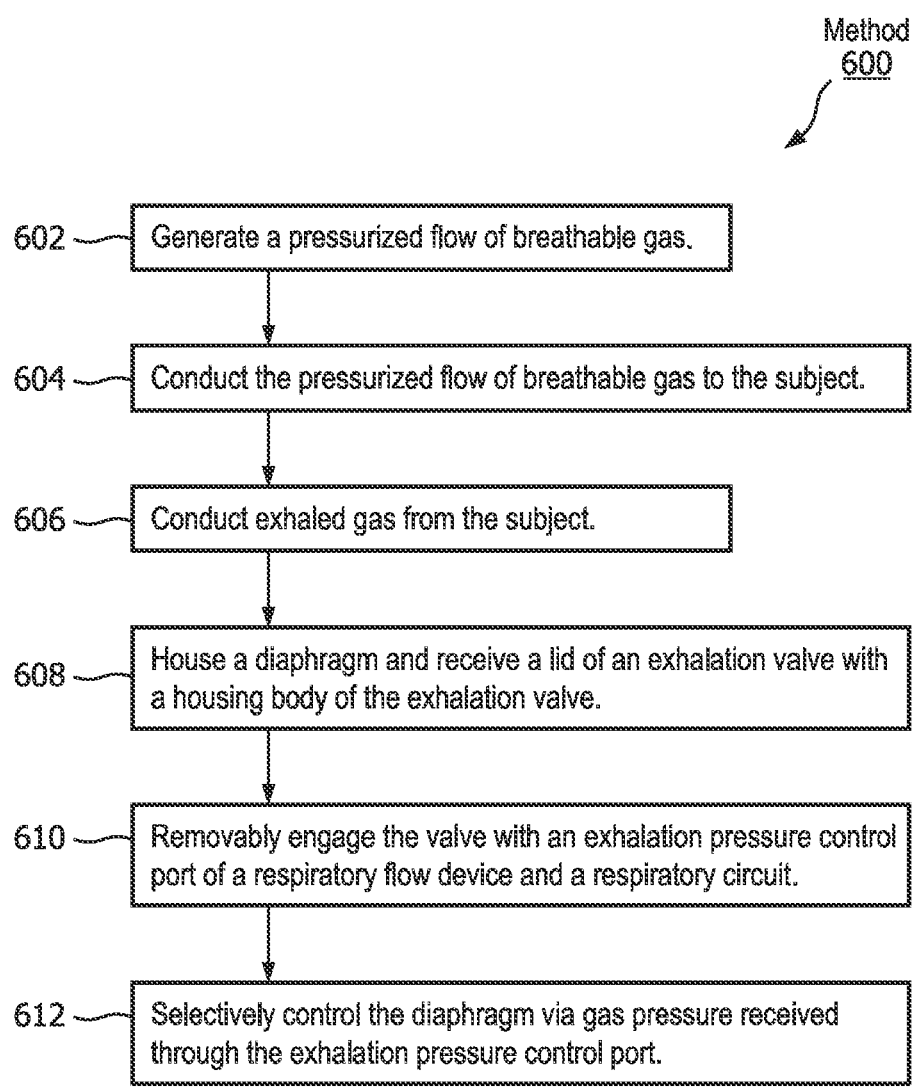
FIG. 6 illustrates a method for providing pressure support to a subject.

FIG. 6 illustrates a method 600 for providing pressure support to a subject with a pressure support system. The system comprises a respiratory flow device that includes an exhalation pressure control port, a respiratory circuit, and an exhalation valve that includes a lid, a diaphragm, and a housing body. The housing body comprises a ramped lock. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, a pressurized flow of breathable gas is generated. The pressurized flow of breathable gas is generated in accordance with a pressure support therapy regime. In some embodiments, operation 602 is performed by a respiratory therapy flow device the same as or similar to respiratory therapy flow device 14 (shown in FIG. 1 and described herein).

At an operation 604, the pressurized flow of breathable gas is conducted to the subject. In some embodiments, operation 604 is performed by a respiratory circuit the same as or similar to respiratory circuit 16 (shown in FIG. 1 and described herein). In some embodiments, the respiratory control circuit is a dual-limb active exhalation circuit. In some embodiments, the respiratory control circuit is a single-limb circuit.

At an operation 606, exhaled gas is conducted away from the subject. In some embodiments, operation 606 is performed by a respiratory circuit the same as or similar to respiratory circuit 16 (shown in FIG. 1 and described herein).

At an operation 608, a diaphragm is housed with a housing body of the valve. A lid of the exhalation valve is received with the housing body of the valve. In some embodiments, operation 608 is performed by a housing body the same as or similar to housing body 56 (shown in FIG. 3 and described herein).

At an operation 610, the valve is removably engaged with the exhalation pressure control port of the respiratory flow device. Removably engaging includes coupling, with the ramped lock, the respiratory therapy flow device at the exhalation pressure control port; causing the lid to form a compression seal around the exhalation pressure control port; and causing the diaphragm to form a compression seal with the lid. In some embodiments, the ramped lock is a cam lock. In some embodiments, the ramped lock comprises three individual ramped locks spaced approximately equidistant from each other on an outer circumference of the housing. In some embodiments, operation 610 is performed by a valve and an exhalation pressure control port the same as similar to valve 56 and exhalation pressure control port 40 (shown in FIG. 1 and described herein).

At an operation 612, the diaphragm is selectively controlled such that gas in the respiratory circuit flows to the ambient atmosphere during exhalation by the subject. The diaphragm is selectively controlled via gas pressure received through the exhalation pressure control port. In some embodiments, operation 612 is performed by an exhalation pressure control port the same as or similar to exhalation pressure control port 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system configured to provide pressure support to a subject, the system comprising:
   a respiratory therapy flow device configured to generate a pressurized flow of breathable gas for delivery to an airway of the subject in accordance with a pressure support therapy regime,
   the respiratory therapy flow device including an exhalation pressure control port formed in a housing of the respiratory therapy flow device, the exhalation pressure control port comprising locking features;
   a respiratory circuit configured to conduct the pressurized flow of breathable gas to the subject and conduct exhaled gas from the subject; and
   an exhalation valve configured to be removably engaged with the exhalation pressure control port and the respiratory circuit along a central axis of the valve, the valve comprising a lid, a diaphragm, and a housing body disposed about the axis, the lid comprising a connector orifice configured to couple with the exhalation pressure control port along the axis, wherein the housing body is configured to house the diaphragm and receive the lid, the housing body comprising a lock configured to engage with the locking features of the exhalation pressure port formed in the respiratory therapy flow device such that an engagement between the valve and the exhalation pressure control port along the axis causes the lid to form a compression seal with the exhalation pressure control port, the diaphragm to form a compression seal with the lid, and the diaphragm to be selectively controlled via gas pressure received through the exhalation pressure control port such that gas in the respiratory circuit flows to the ambient atmosphere during exhalation by the subject.

2. The system of claim 1, wherein the respiratory circuit is a dual-limb active exhalation circuit.

3. The system of claim 1, further comprising a pressure control line configured to conduct gas from the exhalation pressure control port to the lid, wherein, responsive to the valve being disengaged from the exhalation pressure control port, the diaphragm is selectively controlled via gas pressure received from the exhalation pressure control port through the pressure control line to allow exhaled gas in the respiratory circuit to flow to ambient atmosphere.

4. The system of claim 1, wherein the valve is configured such that the lock is a ramped lock.

5. The system of claim 4, wherein the ramped lock comprises three individual ramped locks spaced approximately equidistant from each other on an outer circumference of the housing body.

6. The system of claim 1, wherein the valve is configured such that gas flows through the connector orifice of the lid to the diaphragm in the housing body along the axis.

7. The system of claim 1, wherein an outer surface of the lid faces an interior surface of the housing body.

8. A method for providing pressure support with a pressure support system, the system comprising a respiratory flow device that includes an exhalation pressure control port formed in a housing of the respiratory therapy flow device, the exhalation pressure control port comprising locking features, a respiratory circuit, and an exhalation valve that includes a lid, a diaphragm, and a housing body, the housing body comprising a lock, the lid comprising a connector orifice configured to couple with the exhalation pressure control port along a central axis of the valve, the method comprising:
   generating, with the respiratory therapy flow device, a pressurized flow of breathable gas for delivery to an airway of the subject in accordance with a pressure support therapy regime;
   conducting, with the respiratory circuit, the pressurized flow of breathable gas to the subject;
   conducting, with the respiratory circuit, exhaled gas from the subject;
   housing the diaphragm and receiving the lid with the housing body, the lid, the diaphragm, and the housing body positioned about the axis of the valve;
   removably engaging the valve with the exhalation pressure control port and the respiratory circuit along the axis of the valve, wherein removably engaging includes:
   engaging the lock with the locking features of the exhalation pressure control port formed in the respiratory therapy flow device;
   causing the lid to form a compression seal with the exhalation pressure control port; and
   causing the diaphragm to form a compression seal with the lid; and
   selectively controlling the diaphragm via gas pressure received through the exhalation pressure control port such that gas in the respiratory circuit flows to the ambient atmosphere during exhalation by the subject.

9. The method of claim 8, wherein the respiratory circuit is a dual-limb active exhalation circuit.

10. The method of claim 8, further comprising conducting gas from the exhalation pressure control port to the lid with a pressure control line, and, responsive to the valve being disengaged from the exhalation pressure control port, selectively controlling the diaphragm via gas pressure received from the exhalation pressure control port through the pressure control line to allow exhaled gas in the respiratory circuit to flow to ambient atmosphere.

11. The method of claim 8, wherein the valve is configured such that the lock is a ramped lock.

12. The method of claim 11, wherein the ramped lock comprises three individual ramped locks spaced approximately equidistant from each other on an outer circumference of the housing body.

13. The method of claim 8, wherein gas flows through the connector orifice of the lid to the diaphragm in the housing body along the axis.

14. The method of claim 8, wherein an outer surface of the lid faces an interior surface of the housing body.

15. A pressure support system configured to provide pressure support to a subject, the system comprising:
   means for generating a pressurized flow of breathable gas for delivery to an airway of the subject in accordance with a pressure support therapy regime, the means for generating including an exhalation pressure control port formed in a housing of the means for generating a pressurized flow of breathable gas, the exhalation pressure control port comprising locking features;
   means for conducting the pressurized flow of breathable gas to the subject and conducting exhaled gas from the subject; and
   means for removably engaging with the exhalation pressure control port and the means for conducting along a central axis of the mean for removably engaging, the means for removably engaging comprising a lid, a diaphragm, and a housing body positioned about the axis, the lid comprising a connector orifice configured to couple with the exhalation pressure control port along with axis, wherein the housing body is configured to house the diaphragm and receive the lid, the housing body comprising a lock configured to engage with the locking features of the exhalation pressure port formed in the means for generating such that an engagement between the means for removably engaging and the exhalation pressure control port along the axis causes the lid to form a compression seal with the exhalation pressure control port, the diaphragm to form a compression seal with the lid, and the diaphragm to be selectively controlled via gas pressure received through the exhalation pressure control port such that gas in the means for conducting flows to the ambient atmosphere during exhalation by the subject.

16. The system of claim 15, wherein the means for conducting is a dual-limb active exhalation circuit.

17. The system of claim 15, further comprising means for conducting gas from the exhalation pressure control port to the lid, wherein, responsive to the means for removably engaging being disengaged from the exhalation pressure control port, the diaphragm is selectively controlled via gas pressure received from the exhalation pressure control port through the means for conducting gas from the exhalation pressure control port to the lid to allow exhaled gas in the means for conducting to flow to ambient atmosphere.

18. The system of claim 15, wherein the means for removably engaging is configured such that the lock is a ramped lock.

19. The system of claim 18, wherein the ramped lock comprises three individual ramped locks spaced approximately equidistant from each other on an outer circumference of the housing body.

20. The system of claim 15, wherein the means for removably engaging is configured such gas flows through the connector orifice of the lid to the diaphragm in the housing body along the axis.

21. The system of claim 15, wherein an outer surface of the lid faces an interior surface of the housing body.

\* \* \* \* \*